US009622812B2

(12) United States Patent
Arts et al.

(10) Patent No.: US 9,622,812 B2
(45) Date of Patent: Apr. 18, 2017

(54) ELECTROSURGICAL CANNULAS, SYSTEMS AND METHODS (75) Inventors: Gene H. Arts, Berthoud, CO (US); Jose D. Sartor, Longmont, CO (US)

(73) Assignee: COVIDIEN AG, Neuhausen am Rheinfall (CH)

(*) Notice: Subject to any disclaimer, the term of this patent is extended or adjusted under 35 U.S.C. 154(b) by 2351 days.

(21) Appl. No.: 11/391,901

(22) Filed: Mar. 29, 2006

(65) Prior Publication Data
US 2006/0224156 A1 Oct. 5, 2006

Related U.S. Application Data (60) Provisional application No. 60/666,831, filed on Mar. 31, 2005.

(51) Int. Cl.
*A61B 18/14* (2006.01)
*A61B 18/00* (2006.01)

(52) U.S. Cl.
CPC ...... *A61B 18/1477* (2013.01); *A61B 2018/00821* (2013.01)

(58) Field of Classification Search
CPC ... A61B 2018/00791; A61B 2018/00821; A61B 2018/1425; A61B 18/14; A61B 18/1477
USPC ........................................ 606/41, 28, 31, 44
See application file for complete search history.

(56) References Cited

U.S. PATENT DOCUMENTS

| | | | |
|---|---|---|---|
| 3,435,400 A * | 3/1969 | Beckman ..................... 338/28 |
| 4,922,910 A | 5/1990 | Kanai et al. | |
| 5,807,395 A * | 9/1998 | Mulier et al. .................. 606/41 |
| 6,120,520 A * | 9/2000 | Saadat et al. ................. 606/170 |
| 6,506,189 B1 * | 1/2003 | Rittman et al. ................ 606/41 |
| 6,530,922 B2 | 3/2003 | Cosman et al. | |
| 6,575,969 B1 | 6/2003 | Rittman, III et al. | |
| 6,622,731 B2 * | 9/2003 | Daniel et al. ................. 128/898 |
| 2002/0111608 A1 * | 8/2002 | Baerveldt et al. ............... 606/6 |
| 2002/0188247 A1 * | 12/2002 | Peery ............................. 604/60 |
| 2003/0208197 A1 * | 11/2003 | Wood ............................ 606/41 |
| 2003/0212394 A1 * | 11/2003 | Pearson et al. ................ 606/41 |
| 2004/0267326 A1 | 12/2004 | Ocel et al. | |
| 2005/0059966 A1 | 3/2005 | McClurken et al. | |

FOREIGN PATENT DOCUMENTS

WO    WO 95/20360    8/1995

OTHER PUBLICATIONS

International Search Report from EP 06 00 6963 dated Jul. 25, 2006.
First Australian Examiner's Report dated Nov. 1, 2010.

* cited by examiner

*Primary Examiner* — Linda Dvorak
*Assistant Examiner* — Samantha Good (57) ABSTRACT

Electrosurgical cannulas for use with an electrosurgical generator to thermally treat tissue are disclosed. An electrosurgical cannula for use with an electrosurgical generator to treat tissue is provided. The electrosurgical cannula includes a cylindrical body portion defining a lumen therethrough. The body portion includes a non-coring pointed distal tip which is electrically conductive. The electrosurgical cannula further includes at least one thermocouple having a distal end connected to the conductive distal tip.

15 Claims, 4 Drawing Sheets

ELECTROSURGICAL CANNULAS, SYSTEMS AND METHODS

CROSS-REFERENCE TO RELATED APPLICATION

The present application claims the benefit of and priority to U.S. Provisional Application Ser. No. 60/666,831, filed on Mar. 31, 2005, the entire content of which is incorporated herein by reference.

BACKGROUND

Technical Field

The present disclosure relates generally to cannulas, systems and methods of using the same and, more particularly, to electrosurgical cannulas, systems and methods of using the same in tissue treatment and pain management procedures for intervertebral discs, the nerves surrounding the spinal column and the like.

Background of Related Art

The use of thermal therapy in and around the spinal column, including intervertebral discs and the nerves surrounding the spinal column, is known. Also, the insertion of a cannula either into the intervertebral discs or into the nerves surrounding the spinal column is commonly done for injection of contrast mediums to implement X-ray discograms and for introduction of needle electrode probes therein. This technique is used to detect or diagnose abnormalities or damage to the intervertebral disc and to thermally treat the intervertebral disc or the nerves surrounding the spinal column.

Pain can be derived from degeneration or compression of the intervertebral disc in its posterior or posterior/lateral portions. There is some innervation of the intervertebral disc near the surface of the disc, within its outer portion known as the annulus fibrosus, as well as around the spinal column.

A concern with the use of a cannula, catheter and the like for performing the thermal treatment is the coring of tissue which occurs upon the insertion of the cannula into the target treatment site. In order to prevent the coring of tissue an obturator or a stylet is positioned within the lumen of the cannula in order to occlude the cannula and thus prevent the coring of the tissue. In so doing, the treatment procedure requires the removal of the obturator or stylet from the cannula and introduction of an electrode probe into the cannula and distally to the target treatment site. As can be appreciated, such a procedure requires numerous steps and thus is relatively time consuming.

SUMMARY

According to one aspect of the present disclosure an electrosurgical cannula for use with an electrosurgical generator to treat tissue is provided. The electrosurgical cannula includes a cylindrical body portion defining a lumen therethrough. The body portion includes a non-coring pointed distal tip that is electrically conductive. The electrosurgical cannula further includes at least one thermocouple having a distal end connected to the conductive distal tip.

According to another aspect of the present disclosure, an electrosurgical system for thermally treating tissue is provided. The electrosurgical system includes an electrosurgical generator for supplying an output voltage and an electrosurgical cannula. The electrosurgical cannula includes a cylindrical body portion defining a lumen therethrough. The body portion includes a non-coring pointed distal tip that is electrically conductive. The electrosurgical system further includes at least one thermocouple having a distal end connected to the conductive distal tip and a proximal end connected to the electrosurgical generator. The electrosurgical system still further includes an electrical connection connecting the conductive distal tip of the cannula to a desired output voltage of the electrosurgical generator.

According to another aspect of the present disclosure, a method of performing a thermal treatment of tissue in a patient is provided. The method includes the step of providing an electrosurgical system. The electrosurgical system includes an electrosurgical generator for supplying an output voltage and an electrosurgical cannula. The electrosurgical cannula includes a cylindrical body portion defining a lumen therethrough. The body portion includes a non-coring pointed distal tip that is electrically conductive. The electrosurgical cannula further includes at least one thermocouple having a distal end connected to the conductive distal tip and a proximal end connected to the electrosurgical generator. The electrosurgical system further includes an electrical connection connecting the conductive distal tip of the cannula to a desired output voltage of the electrosurgical generator.

The method further includes the steps of inserting the conductive distal tip of the cannula into a target region, confirming the location of the conductive distal tip of the cannula by activating the stimulate mode of the electrosurgical generator, and treating the target tissue by activating an RF mode of the electrosurgical generator.

It is an advantage of the present disclosure to provide an electrosurgical cannula having a non-coring distal tip.

It is a further advantage of the present disclosure to provide an electrosurgical cannula that can be introduced percutaneously into a target site without having a stylet or obturator operatively disposed within a lumen thereof to occlude the lumen during introduction of the cannula into the target site.

It is still a further advantage of the present disclosure to provide an electrosurgical cannula that can be used to thermally treat tissue without the need to introduce an electrosurgical needle or probe into the cannula or through the cannula following introduction of the cannula into the target site.

BRIEF DESCRIPTION OF THE DRAWINGS

Various preferred embodiments of the presently disclosed systems, devices and methods are disclosed herein with reference to the drawings wherein.

DETAILED DESCRIPTION OF EMBODIMENTS

Figure 1:
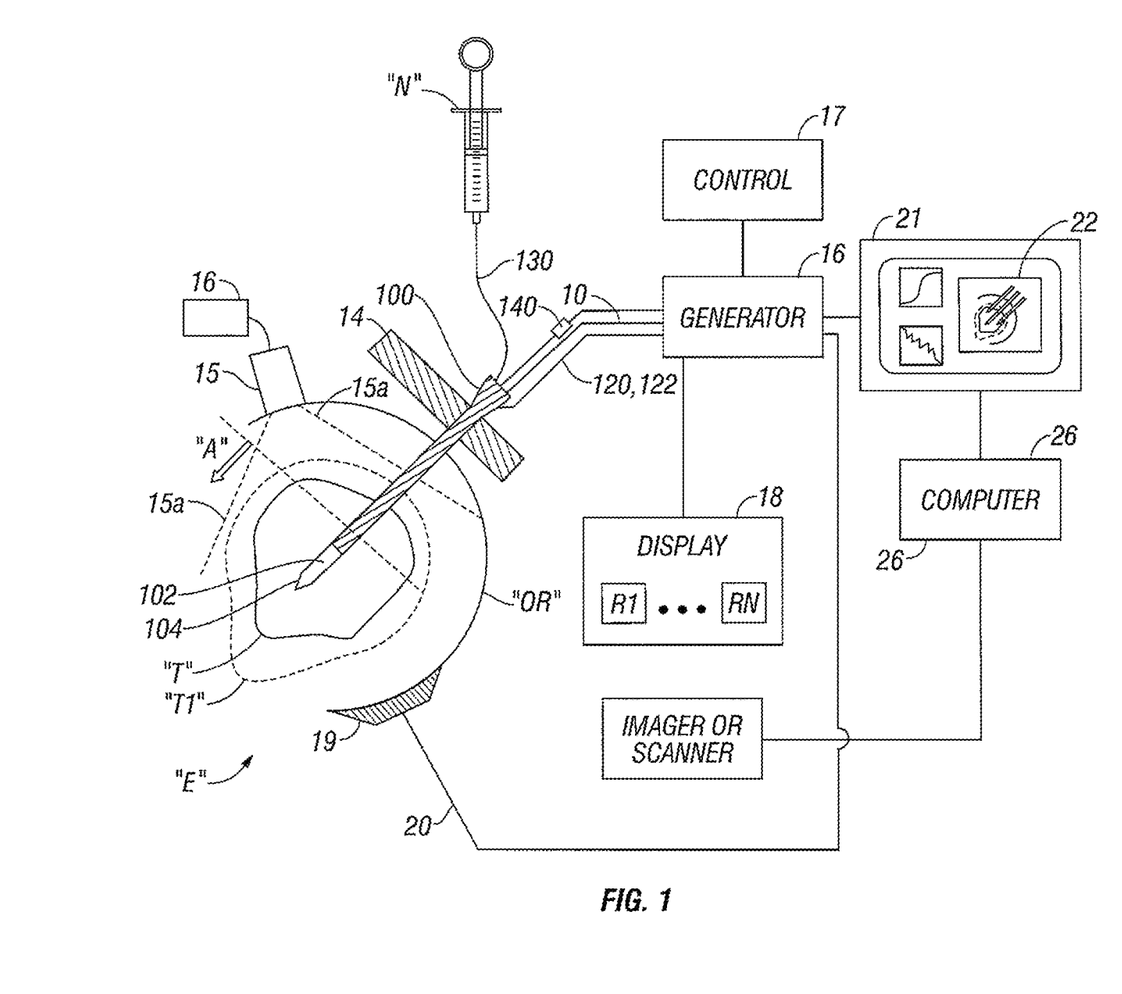
FIG. 1 is a schematic illustration of an electrosurgical system including a cannula according to one embodiment of the present disclosure.

Referring initially to FIG. 1, an embodiment of an electrosurgical system, in accordance with the present disclosure, is generally designated "E". Electrosurgical system "E" includes an electrosurgical cannula 100, which is to be inserted into an organ "OR" of a human body or any other body tissue. As will be discussed in greater detail below, a distal tip 104 of cannula 100 is uninsulated and conductively exposed so that electrical currents induce heating within the tissue or organ "OR". A targeted volume of tissue "T" is shown in sectional view and may represent, for example, a tumor or other abnormality in a human body, the neurological target ganglion or nerve branch of the spinal cord.

Cannula 100 is connected by a wire or cable 10 to an electrosurgical generator 16. Electrosurgical generator 16 may be a radiofrequency or high frequency type generator. Electrosurgical generator 16 includes control elements, illustrated by block 17, which may, for example, increase the radiofrequency power output of cannula 100, control temperature when electrosurgical system "E" or satellite sensors (not shown) include temperature sensors, monitor or control impedance, power, current, voltage, or other output parameters. Electrosurgical generator 16 may include a display or screen, illustrated by block 18, within it or as a separate system, for providing a display of heating parameters, such as temperature for cannula 100, impedance, power, current, or voltage of the radiofrequency output. Such individual display readings are illustrated by the reference letters R1 . . . RN.

Electrosurgical system "E" further includes a reference or return electrode 19, which may be placed in contact with the skin of a patient or an external surface of organ "OR" with a connection 20 to electrosurgical generator 16. Return electrode 19 and connection 20 serve as a path for return current from electrosurgical generator 16 through cannula 100.

By way of example only and in no way to be considered as limiting, electrosurgical generator 16 may be a radiofrequency generator with frequency between about 100 kilohertz (kHz) to several hundred megahertz (MHz). Additionally, electrosurgical generator 16 may have power output ranging from several milliwatts to several hundred watts, depending on the clinical application.

As seen in FIG. 1, by way of illustration only, a targeted region to be thermally treated is represented in sectional view by the line "T". It may be desired to thermally treat the targeted region "T" by fully engulfing targeted region "T" in a volume of therapeutic heat elevation. For example, CT, MRI, or ultrasonic image scanners may be used, and the image data transferred to a data processor or computer 26. As an alternate example, an ultrasonic scanner head 15 may be disposed in contact with organ "OR" to provide an image illustrated by lines 15A. Data processor 26 may be connected to the display devices 18 to visualize targeted region "T" and/or treatment zone "T1" in real-time during the thermal treatment procedure.

As seen in FIG. 1, a handswitch 140 may be electrically disposed between cannula 100 and generator 16. Handswitch 140 functions to activate and de-activate cannula 100. In one embodiment, handswitch 140 may be supported on cannula 100. By placing handswitch 140 on cannula 100 or at a location between cannula 100 and generator 16, handswitch 140 may be manipulated from within the sterile field. Handswitch 140 may be a button, slide or the like supported on cannula 100, disposed along a cord extending between cannula 100 and generator 16, or supported on the end of an electrical tether extending from generator 16.

The image representation of the scan may be displayed on display unit 21, which may, for example, be a CRT or LCD screen. Slice renderings through organ "OR" may be displayed in window 22 to represent the size and position of target region "T". Placement of cannula 100 may be predetermined based on such image data as interactively determined by real-time scanning of organ "OR". Cannula 100 may be inserted into the tissue via any suitable method, such as a freehand technique, by a guide block or introducer 14, or by stereotactic frame or frameless guidance, as known by those skilled in the art.

By way of example, in FIG. 1, dashed line "T1" represents the treatment zone isotherm in a sectional view through organ "OR". Such a treatment zone isotherm may be that of the surface achieving possible temperatures of approximately 98.6° F. or greater for treatment of dorsal root ganglion. At that temperature range, sustained for approximately 30 seconds to approximately several minutes, tissue cells will be thermally treated and branch nerves may be thermally treated or ablated. The shape and size of the treatment volume, as illustrated by dashed line 8, may accordingly be controlled by the orientation of cannula 100, the geometry of distal tip 104, the amount of RF power applied, the time duration that the power is applied, the cooling of cannula 100, etc.

Figure 2:
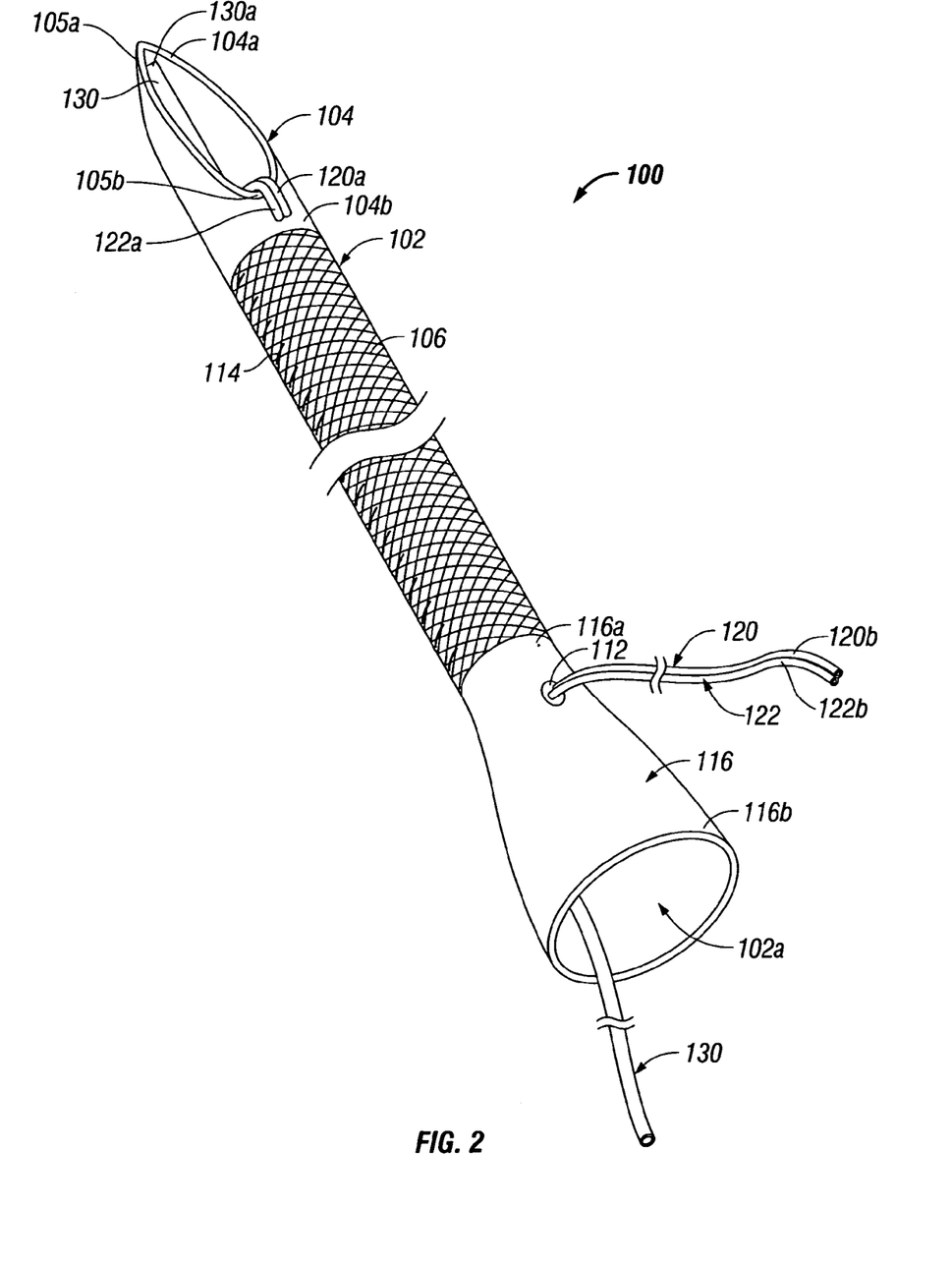
FIG. 2 is a perspective view of an electrosurgical cannula in accordance with an embodiment of the present disclosure.
Figure 3:
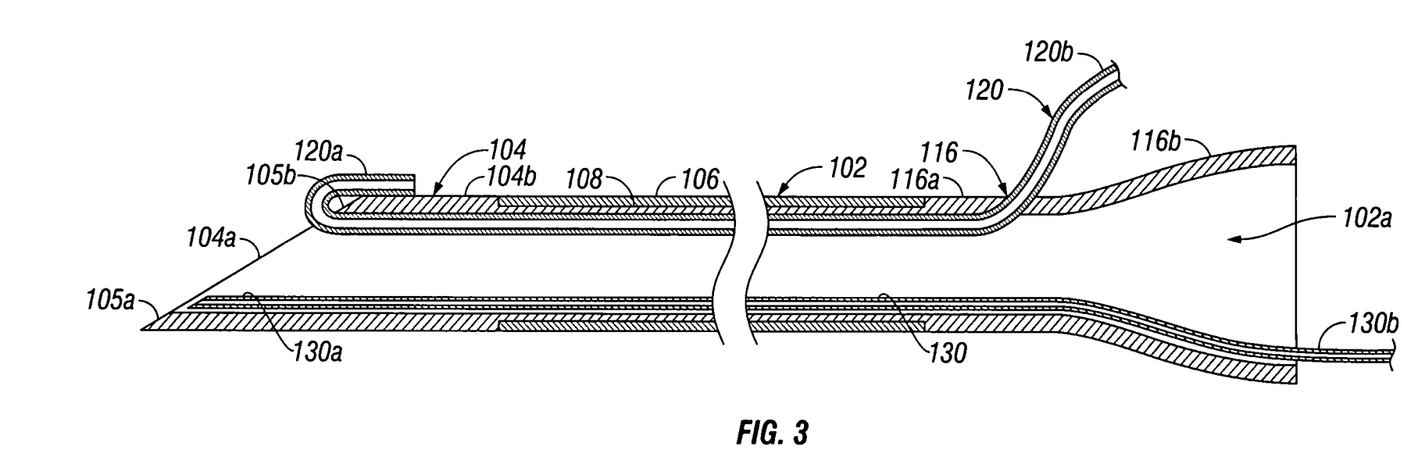
FIG. 3 is a longitudinal cross-sectional view of the electrosurgical cannula of FIG. 1.

Turning now to FIGS. 2 and 3, cannula 100 includes a rigid body portion 102 that enables cannula 100 to be easily urged into the body tissue or organ "OR". Body portion 102 of cannula 100 is desirably substantially cylindrical, defining a lumen 102a therethrough. In one embodiment, body portion 102 is formed from an electronically conductive material, such as, for example, stainless steel and the like.

Body portion 102 of cannula 100 terminates in a tapered or pointed distal tip 104 including a penetration portion 104a and a transition portion 104b. Penetration portion 104a includes a distal edge 105a and a proximal edge 105b. It is within the scope of the present disclosure for at least a portion of the external surface of body portion 102 to be covered with an insulating material 106 (e.g., silicone rubber, etc.), as indicated by the hatched line area in FIG. 2. In one embodiment, insulating material 106 terminates at transition portion 104b of distal tip 104. Distal tip 104 is connected, through body portion 102, to cable 10, and thereby to electrosurgical generator 16.

In one embodiment, distal tip 104 of tubular body 102 may include echogenic surfaces configured to reflect ultrasound. In this manner, during the initial positioning of distal tip 104 of tubular body 102, the echogenic surfaces provide for better visualization of distal tip 104 of tubular body 102 relative to surrounding and/or adjacent anatomical structures.

In one embodiment, as best seen in FIGS. 2 and 3, body portion 102 may include an elongate annular recess 108 formed in an outer surface thereof. Desirably, recess 108 is configured to contain insulating material 106 therein and provide a smooth transmission from transition portion 104b of distal tip 104 to insulating material 106. In this manner, during use, as cannula 100 is pushed through the skin of the patient, the skin slides smoothly over and along the outer surface thereof.

As seen in FIGS. 2 and 3, cannula 100 further includes at least one thermocouple 120 extending through at least a portion of lumen 102a of body portion 102. Thermocouple 120 includes a distal end 120a extending from distal tip 104 of body portion 102. In one embodiment, distal end 120a of thermocouple 120 defines a hook shape such that a portion thereof may be hooked onto proximal edge 105b of penetration portion 104a of distal tip 104. Distal end 120a of thermocouple 120 may be fixedly secured around proximal edge 105b of distal tip 104 by any suitable method including and not limited to welding, soldering, and the like. By hooking distal end 120a of thermocouple 120 around proximal edge 105b of distal tip 104 and securing distal end 120a thereto, the coring effect typically evidenced by a prior art cannula has been eliminated for cannula 100. In addition, the necessity or need to use a stylet or obturator during insertion of cannula 100 to the target site may be eliminated.

A proximal end 120b of thermocouple 120 extends through lumen 102a of body portion 102 and desirably exits body portion 102 through a port or aperture 112 formed near a proximal end thereof. While proximal end 120b of thermocouple 120 desirably exits through port 112 of body portion 102, it is within the scope of the present disclosure for proximal end 120b of thermocouple 120 to extend through an open proximal end of body portion 102. Cannula 100 may include any suitable number of thermocouples 120.

Proximal end 120b of thermocouple 120 is connectable to electrosurgical generator 16. In this manner, during use, information gathered by distal end 120a of thermocouple 120 is transmitted to electrosurgical generator 16 for processing and analysis. For example, during a surgical procedure, as will be described in greater detail below, thermocouple 120 monitors for example, the temperature, etc., at or near distal tip 104 of tubular body 102.

As seen in FIGS. 2 and 3, cannula 100 further includes at least one wire 122 electrically connected to distal tip 104 of body portion 102 to deliver RF power at least to distal tip 104. In one embodiment, wire 122 may include a distal end 122a defining a hook shape such that a portion thereof may be hooked onto proximal edge 105b of penetration portion 104a of distal tip 104, and a proximal end 122b extending through lumen 102a of body portion 102 and exiting out of body portion 102 through aperture 112 thereof. Proximal end 122b of wire 122 is electrically connected to or connectable to electrosurgical generator 16. While distal end 122a of wire 122 is shown and described as being electrically connected to distal tip 104 of cannula 100, it is within the scope of the present disclosure for distal end 122a of wire 122 to be electrically connected to any electrically conductive portion of cannula 100, including body portion 102, so long as said portion of cannula 100 is itself electrically conductive and is in electrical communication with distal tip 104 thereof.

In operation, after distal tip 104 of cannula 100 has been suitably positioned at the target tissue site, distal tip 104 of cannula 100 may be activated to deliver a therapeutic effect to tissue "T". By electrically connecting distal tip 104 of cannula 100 to electrosurgical generator 16, the need for separately introducing an electrosurgical needle or probe into cannula 100 to therapeutically treat tissue "T" has been eliminated.

As seen in FIG. 2, cannula 100 may include metrical markers 114 provided on an outer surface thereof, desirably along an entire length thereof. During use, metrical markers 114 provide the user with an indication of the depth of distal tip 104 of tubular body 102 relative to the outer surface of the patient's skin.

In one embodiment, cannula 100 may include an articulated distal tip 104. In this manner, the insertion of distal tip 104 of cannula 100 into target region "T" may be eased.

In one embodiment, cannula 100 includes a luer hub 116 connected to a proximal end 110 of tubular body 102. Luer hub 116 is configured to flare or radially expand in a proximal direction. In particular, luer hub 116 includes a distal portion 116a having a diameter substantially equal to a diameter of body portion 102 and a proximal portion 116b having a diameter that is larger than the diameter of body portion 102.

As seen in FIGS. 2 and 3, a fluid conduit 130 may be provided that extends through lumen 102a of body portion 102. Desirably, conduit 130 provides a passage for transmission of fluid (e.g., air, $CO_2$, water, saline, blood, etc.) through cannula 100 into and out of the patient's body. Conduit 130 includes a distal end 130a positioned in close proximity to distal tip 104 of cannula 100, and a proximal end 130b extending proximally from cannula 100. By placing distal end 130a of conduit 130 in close proximity to distal tip 104 of cannula 100 the fluid is generally transmitted in a proximal direction out of cannula 130.

Figure 4:
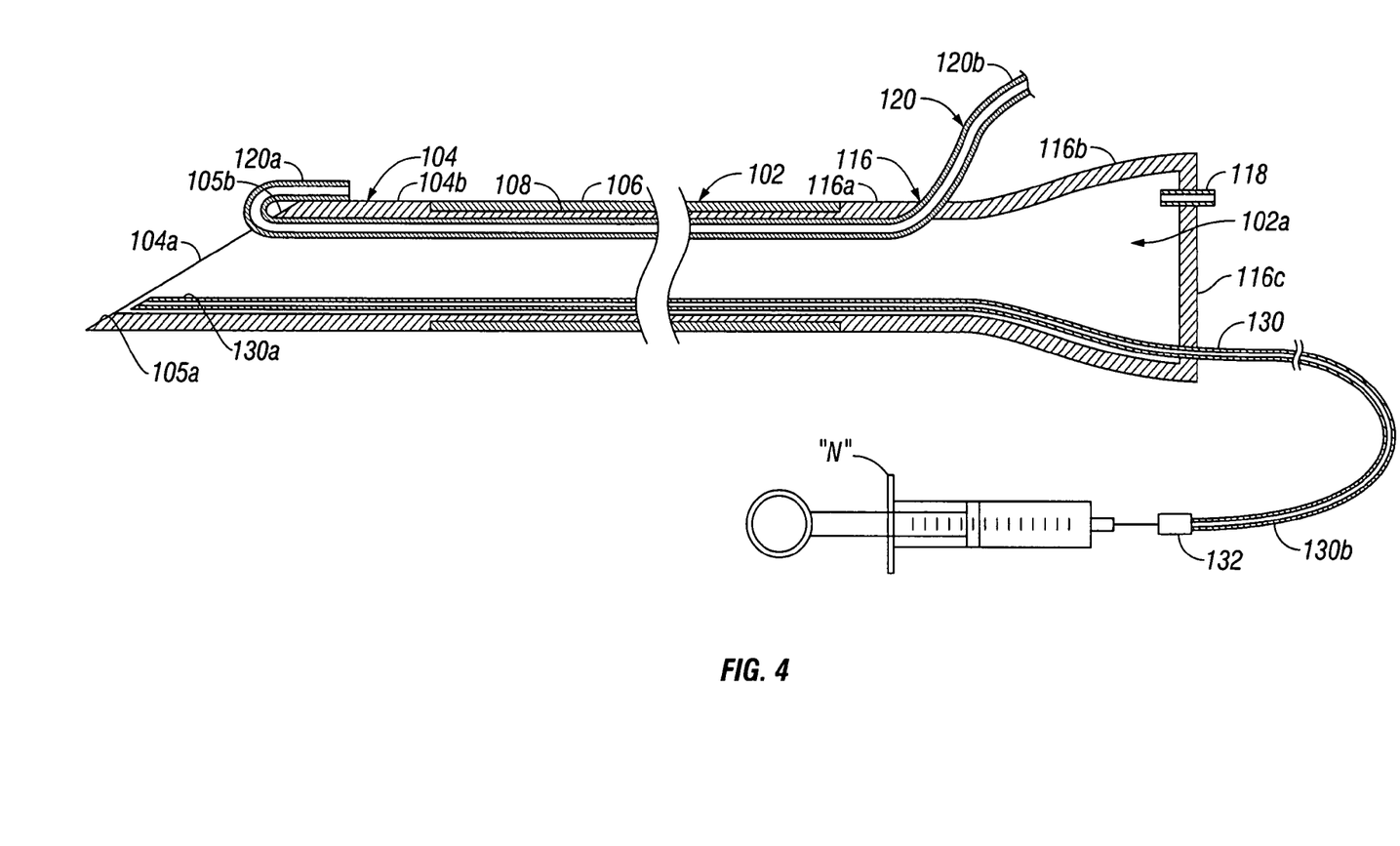
FIG. 4 is a longitudinal cross-sectional view of an electrosurgical cannula according to another embodiment of the present disclosure.

In one embodiment, as seen in FIG. 4, luer hub 116 includes a rear wall 116c for closing off lumen 102a of cannula 100. A venting tube 118 may be placed in rear wall 116c of luer hub 116 in order to provide a passage through which the fluid delivered to distal tip 104 of cannula 100, by conduit 130, may exit. While a venting tube 118 is shown and described, any suitable configuration enabling passage of fluid through rear wall 116c is contemplated, including and not limited to an aperture or the like.

With continued reference to FIG. 4, a luer lock 132 may be provided on proximal end 130b of conduit 130. Luer lock 132 enables syringe or needle "N" to be injected therein to deliver a fluid to conduit 130.

In many procedures and applications (e.g., therapeutic thermal tissue treatment procedures), placement of multiple cannulas, e.g., 2, 3 or more cannulas, into the target treatment site is required. Accordingly, use of cannulas 100, in accordance with the present disclosure, for the procedure will enable the surgeon to simplify the process by reducing the number of steps required to perform the procedure.

In particular, for example, the procedure requires the steps of: inserting cannula 100 into a target region "T", activating a "stimulate mode" on electrosurgical generator 16, desirably from a sterile field; precisely locating distal tip 104 of tubular body 102 of cannula 100 in the target region "T", injecting an anesthetic into the target region "T", re-activating the "stimulate mode" of electrosurgical generator 16 to reaffirm the position of distal tip 104 of body portion 102 of cannula 100, and activating an "RF mode" on electrosurgical generator 16 to treat the tissue while monitoring the temperature.

In one embodiment, the "RF mode" may be activated from within the sterile field by handswitch 140 (see FIG. 1) in the manner described above. In this manner, the operator or surgeon does not have to manipulate generator 16 that may be located outside of the sterile field or instruct a technician who is outside of the sterile field in order to manipulate generator 16.

In one embodiment, the procedure utilizing cannula 100 does not require the separate introduction of an electrosurgical needle or probe through cannula in order to effectuate the treatment of the target region "T".

During activation of the "RF mode" on electrosurgical generator 16, thermocouple 120 monitors the temperature at or around distal tip 104 of tubular body 102 of cannula 100 and transmits such temperature readings to electrosurgical generator 16 and/or to computer 26. Electrosurgical generator 16 and/or computer 26 includes an algorithm that compares the transmitted temperature readings against threshold levels of temperature and adjusts the output parameters to distal tip 104 of cannula 100 accordingly. The threshold levels of temperature have been previously determined and stored in electrosurgical generator 16 and/or computer 26.

In particular, high frequency power from electrosurgical generator 16 may be applied, via cable 10 and/or wire 122, to distal tip 104 of cannula 100. The level of high frequency power is increased according to empirical or pre-planned parameters. This increase may be done either manually or automatically. The process may be controlled according to a microprocessor control within electrosurgical generator 16. The rise in power may be controlled according to measurement, as performed by thermocouple 120, of temperature, impedance, or other suitable feedback parameters associated with the radiofrequency lesion process.

An algorithm determines if the applied power to cannula 100 has exceeded the desired value based on temperature monitoring or a pre-plan. If so, the power may be reduced. If not, other parameters may be monitored, such as, for example, impedance, or direct visualization of the lesion size. If these parameters, such as impedance, are within acceptable limits, power may be increased. As discussed above, the temperature of distal tip 104 of cannula 100 is monitored by thermocouple 120. If the monitored temperatures remain within acceptable levels or are below a targeted temperature or level, the RF power may be increased or modified as needed and/or desired.

Other suitable criteria or parameter choices may be substituted for power as the controlling parameter. For example, as the controlling parameter, the operator may measure, set, vary, or otherwise moderate the current, voltage, impedance, or temperature delivered to distal tip 104 of cannula 100. The current or power output to distal end 104 of cannula 100 may be controlled or held constant. The choice of which generator output parameter is used may vary depending on the clinical need or experience of the surgeon.

The process may be repeated for each cannula 100 until the necessary and/or desired thermal treatment of organ "OR", as indicated by treatment zone "T1", is achieved. While multiple cannulas 100 simultaneously inserted into target region "T" is desired, it is within the scope of the present disclosure for a single cannula 100 to be repeatedly inserted, at various locations, into target region "T" in order to achieve the necessary and/or desired thermal treatment or therapeutic effect.

Variations in the placement and geometry of cannula 100, such as parallel or non-parallel, may be used to create changes in the shape of the treatment volume and needed and/or desired. Insertion of cannula 100 from varied directions may help in avoiding critical anatomical structured or obstructions while still increasing the numbers of cannula 100 inserted in order to achieve the size of the treatment zone.

Variations in the degree or size of distal tip 104 of cannula 100 may vary according to the particular target region "T" being affected. Additionally, cannula 100 may be configured to have any suitable length.

Variations in the choice of electrical output parameters from the electrosurgical generator, to control or monitor the treatment process, may vary widely depending on the operator's experience, technique, or preference. For example, a common RF voltage may be applied to all of cannulas 100 simultaneously. As an alternate embodiment, in accordance with the present disclosure, the clinician may choose to control the RF current to the individual cannulas 100 or the total current of all the cannulas 100 combined. Voltage variations on each cannula 100 could be applied to achieve constant current output from each cannula 100. Alternatively, constant power output from each cannula 100 may be sought in some clinical settings. Voltage variations or phases between cannulas 100 may be implemented to achieve desired temperature distribution in the tissue as monitored by temperature sensors (e.g., thermocouples 120) in the tissue or by visualization of temperature distribution using thermally sensitive MRI scanning, for example. Accordingly, the choice of electrical output type, sequence, and levels and the distribution of the cannulas 100 should be considered to have wide variations within the scope of the present disclosure.

In view of the foregoing considerations, as would be apparent by persons skilled in the art, implementations and systems should be considered broadly and with reference to the claims set forth below.

What is claimed is:

1. An electrosurgical cannula for use with an electrosurgical generator to treat tissue, comprising:
    a cylindrical body portion defining a lumen therethrough, the body portion including a non-coring pointed distal tip that includes a penetration portion configured to penetrate tissue and a transition portion configured to connect the penetration portion to a remainder of the body portion, wherein the distal tip is electrically conductive; and
    at least one thermocouple having a distal end connected to the distal tip,
    wherein the penetration portion of the distal tip includes a distal edge and a proximal edge, and wherein the distal end of the thermocouple includes a hook portion fixedly secured to the proximal edge of the penetration portion of the distal tip such that at least a first portion of the distal end of the thermocouple extends distally at least partially along a length of the transition portion and at least a second portion of the distal end of the thermocouple extends proximally along an outer surface of the transition portion, and
    wherein the second portion abuts the outer surface of the transition portion.

2. The electrosurgical cannula according to claim 1, wherein the distal tip is one of electrically connected and electrically connectable to an electrosurgical generator.

3. The electrosurgical cannula according to claim 1, wherein the thermocouple is one of electrically connected and electrically connectable to an electrosurgical generator.

4. The electrosurgical cannula according to claim 1, wherein a proximal end of the thermocouple extends through an aperture formed in a proximal end of the body portion.

5. The electrosurgical cannula according to claim 1, wherein the body portion is electrically conductive and includes an insulating material provided over at least a portion thereof and terminating at a location proximal of the distal tip.

6. The electrosurgical cannula according to claim 5, wherein the insulating material is disposed within an annular recess formed in the body portion.

7. The electrosurgical cannula according to claim 1, further comprising a luer connected to a proximal end of the body portion.

8. The electrosurgical cannula according to claim 1, further comprising a fluid conduit extending through the lumen of the body portion, the conduit including a distal end located in close proximity to the distal tip of the cannula.

9. An electrosurgical system for thermally treating tissue, comprising:
    an electrosurgical generator for supplying an output voltage;
    an electrosurgical cannula, including:
        a cylindrical body portion defining a lumen therethrough, the body portion including a non-coring pointed distal tip that includes a penetration portion configured to penetrate tissue and a transition portion configured to connect the penetration portion to a remainder of the body portion, wherein the distal tip is electrically conductive; and at least one thermocouple having a distal end connected to the distal tip, wherein the penetration portion of the distal tip includes a distal edge and a proximal edge, and wherein the distal end of the thermocouple includes a hook portion configured to be fixedly secured to the proximal edge of the penetration portion of the distal tip such that at least a first portion of the distal end of the thermocouple extends distally at least partially along a length of the transition portion and at least a second portion of the distal end of the thermocouple extends proximally along an outer surface of the transition portion, and wherein the second portion abuts the outer surface of the transition portion; and an electrical connection connecting the distal tip of the cannula to a desired output voltage of the electrosurgical generator.

10. The electrosurgical system according to claim 9, wherein a proximal end of the thermocouple extends through the lumen of the body portion and out an aperture formed in a proximal end of the body portion.

11. The electrosurgical system according to claim 9, wherein the body portion is electrically conductive and includes an insulating material provided over at least a portion thereof and terminating at a location proximal of the distal tip.

12. The electrosurgical system according to claim 11, wherein the insulating material is disposed within an annular recess formed in the body portion of the cannula.

13. A method of performing a thermal treatment of tissue in a patient, comprising the steps of:

providing an electrosurgical cannula having:

a cylindrical body portion defining a lumen therethrough, the body portion including a non-coring pointed distal tip that includes a penetration portion configured to penetrate tissue and a transition portion configured to connect the penetration portion to a remainder of the body portion, wherein the distal tip is electrically conductive; and at least one thermocouple having a distal end connected to the distal tip and a proximal end connected to an electrosurgical generator, wherein the penetration portion of the distal tip includes a distal edge and a proximal edge, and wherein the distal end of the thermocouple includes a hook portion fixedly secured to the proximal edge of the penetration portion of the distal tip such that at least a first portion of the distal end of the thermocouple extends distally at least partially along a length of the transition portion and at least a second portion of the distal end of the thermocouple extends proximally along an outer surface of the transition portion, and wherein the second portion abuts the outer surface of the transition portion; and an electrical connection connecting the distal tip of the cannula to a desired output voltage of the electrosurgical generator;

inserting the distal tip of the cannula into a target region;

locating the distal tip of the cannula in the target region by activating a stimulate mode of the electrosurgical generator;

confirming the location of the distal tip of the cannula by re-activating the stimulate mode of the electrosurgical generator; and treating the target tissue by activating an RF mode of the electrosurgical generator.

14. The method according to claim 13, further comprising the step of injecting an anesthetic into the target region prior to confirming the location of the distal tip.

15. The method according to claim 13, further comprising the step of monitoring at least one of temperature and impedance at the target region.

* * * * *

UNITED STATES PATENT AND TRADEMARK OFFICE
CERTIFICATE OF CORRECTION

| | | |
|---|---|---|
| PATENT NO. | : 9,622,812 B2 | Page 1 of 1 |
| APPLICATION NO. | : 11/391901 | |
| DATED | : April 18, 2017 | |
| INVENTOR(S) | : Gene H. Arts and Joe D. Sartor | |

It is certified that error appears in the above-identified patent and that said Letters Patent is hereby corrected as shown below:

On the Title Page

Item (75) the second inventor should be listed as:
"Joe D. Sartor"

Signed and Sealed this
Eleventh Day of July, 2017

Joseph Matal
*Performing the Functions and Duties of the*
*Under Secretary of Commerce for Intellectual Property and*
*Director of the United States Patent and Trademark Office*